United States Patent
Strelchenok

(12)
(10) Patent No.: US 6,599,507 B2
(45) Date of Patent: Jul. 29, 2003

(54) COMPOSITION FOR THE TREATMENT OF IMMUNE DEFICIENCIES AND METHODS FOR ITS PREPARATION AND USE

(75) Inventor: Oleg Strelchenok, Lidingo (SE)

(73) Assignee: Ardenia Investments, Ltd. (GI)

( * ) Notice: Subject to any disclaimer, the term of this patent is extended or adjusted under 35 U.S.C. 154(b) by 0 days.

(21) Appl. No.: 09/738,704

(22) Filed: Dec. 15, 2000

(65) Prior Publication Data

US 2001/0034324 A1 Oct. 25, 2001

Related U.S. Application Data

(63) Continuation of application No. PCT/EP99/04201, filed on Jun. 17, 1999.

(30) Foreign Application Priority Data

Jun. 17, 1998 (SE) ................................. 9802162

(51) Int. Cl.$^7$ ...................... A61K 39/385; A61K 39/39; C07K 17/00; C07F 9/09
(52) U.S. Cl. ............... 424/193.1; 424/195.11; 530/380; 558/72
(58) Field of Search ....................... 424/193.1; 530/380; 558/72

(56) References Cited

FOREIGN PATENT DOCUMENTS

| WO | WO 98/07752 | 2/1998 |
|---|---|---|
| WO | WO 99/65936 | 12/1999 |

OTHER PUBLICATIONS

Sekiguchi et al, Cancer Chemother Pharmacol 13: 75–77, 1984.*
Iturralde et al, Biochemistry International 20(1): 37–43, 1990.*
Zou et al, Cancer Chemother Pharmacol 39(1–2):103–8, 1996.*
Voelker et al, JAMA 282(21): 1992–94; Dec. 1999.*
Abbas et al, in Cellular and Molecular Immunology, W.B. Saunders Company, p. 245, 1991.*
in The Merck manual of Diagnosis and therapy, Merck Research laboratories, 1999 edition, pp. 1321–1323.*
R. N. K. Carlson et al., "High affinity of α–foetoprotein for arachidonate and other fatty acids", *Biochem J.* (1980) 190, pp. 301–305.
H. F. Deutsch, "Some Biological Roles for α–Fetoprotein Unsaturated Fatty Acid Complexes", DPT of Physiological Chemistry Univ. of Wisc., Part II. Biochem. Analyses of Oncofetal Proteins, 1983, pp. 38–49.
J. M. Torres et al., "Alpha–fetoprotein–Mediated Uptake of Fatty Acids by Human T Lymphocytes", *J. of Cellular Physiology* 150, 1992, pp. 456–462.

* cited by examiner

Primary Examiner—Christina Chan
Assistant Examiner—Phoung N. Huynh
(74) Attorney, Agent, or Firm—Morrison & Foerster LLP

(57) ABSTRACT

A complex of alpha-fetoprotein (AFP) and N-arachidonoyl aminoethyl phosphate (N-AAP) is shown to have significant immunostimulating properties and can therefore be used as a therapeutic agent in various indications, such as immune deficiencies and in particular immune deficiencies related to cancer therapy.

21 Claims, No Drawings

COMPOSITION FOR THE TREATMENT OF IMMUNE DEFICIENCIES AND METHODS FOR ITS PREPARATION AND USE

This application is a continuation application of PCT/EP99/04201 filed Jun. 17, 1999, which claims priority to SE 9802162-9 filed Jun. 17, 1998.

FIELD OF THE INVENTION

This invention relates to a new therapeutic composition, in particular an immunomodulating composition or a composition for uses in the treatment of immune deficiencies. The invention also discloses methods for the preparation of said composition and methods for the therapeutic application of the same.

DESCRIPTION OF THE PRIOR ART

Alpha-fetoprotein (AFP), a protein from mammalian fetal blood, has been held to be of a certain scientific interest since the moment it was first discovered in 1958. The biological properties of this protein are subject of numerous investigations: there is however still no final answer as to the role of this protein in the organism. It is known, that unsaturated fatty acids such as arachidonic and docosahexaenoic acid and their metabolites are characterized as natural AFP ligands and can be detected as complexes with the given protein circulating in blood vessels. However, AFP is not only a transport protein for unsaturated fatty acids. It has also been found that it forms complexes with bilirubin, retinoids and copper. In addition to the transport of low molecular weight substances AFP can take part in immune response regulation. Most of the studies on AFP's immunoregulating properties indicate that the protein has immunosuppressing features.

It should also be pointed out, that practically no data on the immunosuppressing properties of AFP were obtained for the pure protein, but using AFP-enriched sera or amniotic fluid during in vitro experiments. The immunoregulating properties of AFP were shown to be dependent on the origins of the preparations and the purification methods. For example, AFP obtained from fetal liver is characterized by a stronger suppression of mitogene-induced lymphocyte transformation in comparison with AFP, obtained from human blood of patients suffering from primary liver cancer.

At the same time it has been demonstrated, that AFP stimulates tissue regeneration after injuries. AFP tended to decrease the inflammatory processes artificially simulated in animals supposedly by blocking the receptors of immunocompetent cells. It has also recently been shown in a series of experiments, that AFP is actively absorbed by growing and differentiating cells, and this process is controlled by the quantity of expressed AFP-receptors. It was found that intracellular AFP concentration increased simultaneously with the increase of the quantity of AFP-receptors on the surface of proliferating T-lymphocytes and malignant cells. It was stated, based on these data, that this protein functions as a shuttle-transporter, bringing the ligand inside the cell and then returning into intercellular liquid to repeat the cycle (Esteban C., et al., Int. J. Cancer, v.49, p. 425-430, 1991).

The most important ligands transported inside the cell are unsaturated fatty acids, namely arachidonic and docosahexaenoic acid and their metabolites. It is experimentally proven, that the presence of AFP significantly increases the flow of these acids into the cytoplasm of activated T-lymphocytes (Torres J. M., et al., J. Cell. Physiol, v. 150, p.456–462, 1992).

The increase of the concentration of unsaturated fatty acids is of great importance as said acids are not only necessary structural components of the cell membrane, but also serve as an additional source of energy for the cells. The metabolites of these acids, in particular those of arachidonic acid, can act as secondary messengers, thus participating in the regulation of cellular growth and differentiation (Bevan S., et al., Nature (London), v. 328, p. 20, 1987).

Anandamide (arachidonyl-2-ethanolamid) is one of the recently discovered fatty acid metabolites. It is characterized by the high physiological effect targeted to brain. Anandamide is a novel lipid neurotransmitter first isolated from porcine brain. It has been shown to be a functional agonist for cannabinoid CB1 and CB2 receptors. Its presence results in many pharmacological effects caused by delta 9-tetrahydrocannabinol (delta 9-THC). Anandamide parallels delta 9-THC in its specific interaction with the cannabinoid receptor and in the inhibition of adenylate cyclase. For many decades the mechanism of action of cannabinoid compounds, which are structurally similar to delta 9-THC, was unknown. Tremendous progress has recently been made in characterising cannabinoid receptors both centrally and peripherally as well as in studying the role of the second messenger systems at cellular level. Cannabinoid derived drugs have been used for centuries for medicinal purposes. However, these drugs on the market today lack specificity and produce many side effects (Chakrabarti A., et al., Brain. Res. Bull., v.45, 30 p.67–74, 1998).

Anandamide can be formed enzymatically via two separate synthetic pathways in the brain: enzymatic condensation of the free arachidonic acid and ethanolamine; and formation of N-arachidonoyl phosphatidylethanolamine from phosphatidyletanolamine and arachidonic acid esterified at the 1-position of phosphatidylcholine, and subsequent release of anandamide from N-arachidonoyl phosphatydylethanolamine through the action of a phosphodiesterase (phospholipase D) (Suguira T., et al., Eur. J. Biochem., v.240. p.53–62, 1996).

N-acyl-transferase catalyses the transfer of arachidonoyl residue onto the NH2 group of phosphatydylethanolamine. This enzyme is Ca2+dependent and is mostly localised in brain and testis. The pathway of anandamide formation is presented below:

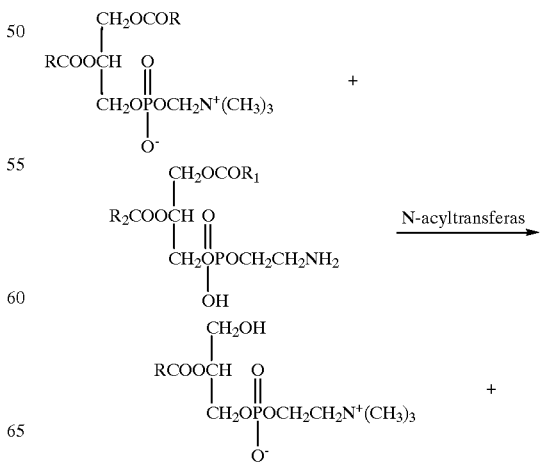

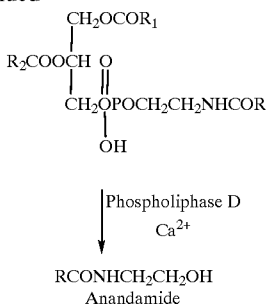

R—Arachidonoyt
$R_1$ and $R_2$—alkyl

N-arachidonoyl phosphatidylethanolamine could also be a substrate for phospholipase C (Brockerhoff H., Jensen R. G., Lipolytic enzymes, Academic press, New York-San Francisco-London, 1974). In this case the enzymatic reaction results in formation of N-arachidonoyl aminoethylphosphate (N-AAP).

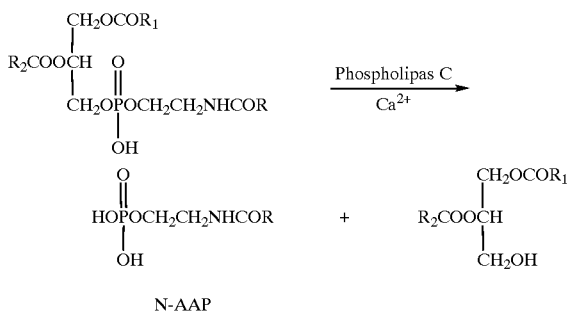

N-AAP

The absence of literature data on N-AAP presence in brain supports the assumption, that this phosphate is unstable and can be quickly transformed to anandamide by endogenous phosphatases during processing of the brain preparations. To study the N-AAP biological activity one has to consider a reversible complex of AFP with N-AAP. In this case N-AAP can be protected by the protein molecule from the enzymatic influence in blood vessels as well as in the other biological liquids.

The idea to use reversible complexes of transport proteins with the conjugates of their natural ligands with drugs to strengthen their pharmaceutical effect and reduce the side effects, particularly during cancer treatment, was first reported in 1958 (Mathe G. et al., C. R. Seances Acad. Sci. v. 246, p. 1626–1628, 1958; Magnenat R. et al., Eur. J. Cancer., v. 5. p. 3340, 1969). The reversible complex of AFP with the conjugates of daunomicin with arachidonic and docosohexaenoic acids appeared to be more effective cytostatic agent for hepatoma AH-66 cells, generating more AFP than the free daunomicin (Deutsch H. F. et al., Cancer Res. v. 43, p.2668–2662, 1983), and the conjugate of 2-deoxy-5-fluorouridine-oleic and docoso hexaenoic acids with AFP had much greater cytotoxic activity for cancer cell lines H 1–29, than the free 2-deoxy-5-fluorouridine (Halmos T. et al., Biochem. Pharmacol v. 44., p. 149–156, 1992).

Some direct immunologic response observations on the role of a factor that appears to be AFP have been reported (Abramsky, O., et al., Isr. Med., vol. 15, p. 943, 1979; Brenner T., et al., Immunol. Lett., vol. 3, p. 163, 1981). They found that what is likely to be fetal AFP prevented the development of myasthenia gravis in rabbits and, furthermore, that clinical signs of the disease in these animals disappeared when they were treated with the assumed AFP. It was shown that experimental allergic encephalomyelitis induced in guinea pigs was successfully treated as well as partially prevented by administration of AFP (Abramsky O., et al., J. Neuroimmunol., vol. 2, p. 1, 1982).

It has thus been shown that AFP, depending on its origin and surrounding conditions, exerts different functions by different mechanisms. Firstly, there is a regulatory effect on the concentration of the unbound form of its various ligands (e.g. fatty acids, estrogens, phytosteroids). It is known, that fatty acids, in particular polyunsaturated fatty acids, modulate positively or negatively many steps of the action of various steroids and many enzymes involved in the transduction of membrane-triggered signals. Secondly, different conformations (holoforms) of AFP, depending on the nature and concentration of the ligand(s) bound to it, might influence the binding of the protein to specific receptor(s) and as a consequence influence it's/their biological properties (internalisation, action on the membrane signal transduction pathway). Thirdly, in addition to the mechanisms proposed above, the protein can exert effects associated with other signals, such as growth factors.

Obviously, there appears to be no uniform and consistent understanding of the mechanisms of AFP. Presently used immunomodulating substances and in particular immunostimulating substances are not without their drawbacks. Interferon preparations give influenza-like symptoms in about 90% of the patients and the risk of other side effects must be considered. Typically, the side effects range from muscle and skeletal soreness and pains, headache and similar symptoms to more serious symptoms as leucopenia, anaemia, trombocytopenia, splenomegalia and hepatomegalia, just to mention some examples.

The aim of the present invention is to make available a new pharmaceutical immunomodulating composition exhibiting improved properties, not only with respect to therapeutical properties such as efficacy and extent of application, but also pharmacological and technical properties such as ease of manufacture, storage, mixing and administration.

SUMMARY OF THE INVENTION

The present invention concerns a therapeutically useful complex, in particular an immunomodulating complex according to the attached claims. The invention will be described in closer detail in the following description and examples.

DESCRIPTION

The invention makes available an equilibrium reversible complex of alpha-fetoprotein and N-arachidonoyl aminoethylphosphate, in particular an equilibrated non-covalent complex of N-arachidonoyl aminoethylphosphate (N-AAP), a metabolite of arachidionic acid and alpha-fetoprotein (AFP) of high purity, for example AFP isolated from human cord blood with more than 99% purity. The chemical structure of the non-protein part of the complex is presented below:

The inventive complex may contain its components in highly varying molar ratios, such as from an equimolar ratio to a significant overabundance of N-AAP in relation to AFP. Normally, the complex contains from 1 up to 300 moles N-AAP per mole AFP. The inventive complex may be obtained by adding an ethanol solution of N-AAP to a diluted water solution of AFP followed by ultrafiltration, said filtration resulting in concentrating the solution and removing the N-AAP that remained unbound to AFP. The AFP concentration in solution varies from 0.1 up to 2 mg/ml and that of N-AAP—from 0.005 up to 30 mg/ml.

In the inventive complex, the protein is reversible linked not to one or several molecules of the ligand but surprisingly with a micelle, containing up to 300 molecules of N-AAP. It is known, that the natural AFP ligands like arachidonic, docosohexaenoic acids, etc. are sparingly soluble in water. If a concentrated ethanol solution of these substances is injected into water under special conditions one obtains a colloid solution. The obtained colloid particles (micelles) contain about from 50 to about 300 or more molecules of the lipid. The addition of unsaturated fatty acids—AFP ligands to AFP water solution results in the formation of protein-lipid complexes. The properties of such complexes have been insufficiently studied, but it is however possible to assume, that their formation occurs not only due to the hydrophobic fragment of the protein molecule but is also stipulated by the participation of AFP's active centre(s). Attempts to produce AFP complexes with other fatty acids, not being the ligands to this protein, namely with other fatty acids, have been unsuccessful. The changes of molecular weight of the protein as judged by gel-filtration is an evidence of the existence of AFP complexes with the micelles of its natural ligands.

In one embodiment, the molecular weight of AFP incorporated in the complex with its natural ligand or its derivative (for example N-AAP) increases by approx. 2 times, while gel-filtration of AFP with palmitoyl acid micelles did not result in the changes of elution volume in comparison with that for free AFP. The micelle contained about 200–300 molecules of lipid. The obtained preparations of AFP complexes with the micelles of its natural ligands are characterized as reversible protein-lipid complexes, but at the same time have the properties of proteoliposomes (Degrip W. J. Biochem J. Mar. 1. 330, p. 667–674, 1998).

In another embodiment, the molecular weight of AFP incorporated in the complex with its natural ligand or its derivative (for example N-AAP) increases by approx. 2–3 times. The micelles contained 100–300 molecules of lipid. The obtained preparations of AFP complexes with the micelles of its natural ligands or metabolites are characterised as reversible protein-lipid complexes, but at the same time have the properties of proteoliposomes.

It has been shown that AFP enter the cells via small vesicles and endosomes and move to multivesicular bodies and tubular vesicular elements located in the Golgi-centrosphere region to be finally recycled back into the medium (Geuskens M., et al. Microsc. Res. Tech. v.28, p. 297–307, 1994).

Based on the literature data and the experimental results obtained by the present inventor it is suggested, that the reversible complexes of AFP with N-AAP penetrates into lymphocytes by means of AFP's receptor intermediated endocytosis. On the one hand, the AFP/N-AAP complex inside lymphocytes could apparently regulate the synthesis of phospholipids as the structural components of cellular membrane. On the other hand N-AAP is a source of arachidonic acid which is further being incorporated into the phospholipid structures.

The influence of AFPIN-AAP complexes as well as their basic components on humoral immune response was estimated by counting the quantity of antibody-forming cells (AFC) in the spleen. It has been experimentally proved that N-AAP in itself does not exhibit immunogenic activity. The relative amount of AFC cells on the 5-th day after N-AAP injection to the animals immunized with sheep erythrocytes was not significantly changed in comparison with control series. Administration of the same dosage of the inventive AFP/N-AAP complex (AFPIN-AAP ratio 1:200) resulted in that the relative amount of AFC increased 87% and the total AFC amount increased 162% on the 5-th day after injection in comparison with the amount of cells in animals immunized only with sheep erythrocytes.

An administration of the inventive complex in AFP/N-AAP ratios of 1:100 or 1:300 showed a slightly decreased immunostimulating activity of the complex. On the 5-th day after injection of a 1:100 complex the apparent AFC amount had increased by 30%, and the total amount by 79%. For a 1:300 complex the increase in apparent AFC amount was 48.3%, and for the total cell amount 103.3%. The results show a significant effect of the complex within the interval 1:100–1:300, with an improved effect corresponding to the AFP/N-AAP ratio 1:200. However, the AFP/N-AAP ratio can be varied within a broader interval, e.g. 1:1–1:10000.

AFP alone, administered in corresponding doses reduces or does not significantly effect the immunogenic characteristics of sheep erythrocytes in mice.

AFP was isolated from human cord blood by immunoaffinity chromatography on monoclonal antibodies against AFP immobilised on Sepharose®, immunoaffinity chromatography on polyclonal antibodies to the proteins of normal human blood and gel-filtration on Sephacryl® S-200. The AFP preparation thus obtained was more than 99% purity and did not contain low molecular weight impurities and retained completely its biological activity.

Other sources of AFP may be purified and/or modified AFP from other mammals, for example from genetically modified mammals, or from cell cultures. Preferably, the AFP is biotechnologically manufactured using a cell culture of genetically modified cells expressing human AFP. With knowledge of the nucleotide sequence coding for human AFP, this can be inserted in a host, together with necessary promoters and other sequence information, for example sequences influencing the extracellular expression of AFP. The AFP is collected from the cell culture and purified by chromatography, and may be further purified by gelfiltration. In any case, the production method must involve steps, which guarantee that the final product is free from pyrogens and possible viral or bacterial contaminants. Suitable production methods can for example be found in the field of interferon production.

According to an embodiment of the invention, the AFP/N-AAP complex is used as a therapeutic agent either as such, or used for the manufacture of a therapeutical preparation, possibly containing other agents. The inventive complex is particularly suitable as an immunostimulating agent, e.g. for the treatment of immune deficiencies. The complex can also be used for the manufacture of an immunostimulating preparation.

According to a preferred embodiment, the inventive complex is used for the treatment of immune disorders associated with cancer therapy. The inventive complex can also be used for the manufacture of a pharmaceutical preparation for the treatment of cancer. Examples of such disorders or immune deficiencies occurring as a consequence of cancer treatment, include neutropenia.

The inventive complex can also be used as a prophylactic agent in patients susceptible for infections, or for the manufacture of a pharmaceutical composition for the treatment of such patients.

Consequently, the invention also concerns methods for the treatment of immune deficiencies, wherein an equilibrium reversible complex according to the present invention is administered to a mammal. Preferably, said complex is administered intravenously.

Medical form preparation: The active composition may be administered intravenously. Alternatively, to simplify storage and handling, the composition can be prepared as a sterile powder for extemporaneous preparation of sterile injectable solutions or dispersions. In all cases the form must be sterile and must be fluid to the extent allowing for easy handling by syringe and similar devices. Further, the preparation must be stable under conditions of manufacture and storage and must be protected against the contaminating action of micro-organisms such as bacteria and fungi.

Sterile injectable solutions are prepared by incorporating AFP and N-AAP in a required amount of water, ultrafiltration (concentration) of the solution followed by filter sterilization. In the case of sterile powders for the preparation of sterile injectable solutions, the preferred methods of preparation are vacuum drying or suitable freeze-drying techniques that yield a powder of the active ingredients from previously sterile filtered solutions thereof.

For direct introduction of a complex to patients a sterilized preparation is first injected in a physiological saline solution (100–500 ml) or in a protein (albumin) solution then intravenously administered to a patient. When a lyophilized preparation is used, it should be previously dissolved in 2–10 ml of sterilized solution (distilled water, physiological saline solution or albumin solution) whereupon the obtained sterilized solution is added to 100–500 ml physiological solution or protein solution for intravenous introduction, same as in case of using the solutions.

The therapeutic effective doses are in interval from 2 mg/kg to 7 mg/kg for N-AAP and from 0.2 mg/kg to 0.7 mg/kg for AFP.

EXAMPLES

Example 1

Human AFP Isolation 1 l human cord blood was incubated for 1 hr at continuous stirring with 25 ml Sepharose® with immobilised monoclonal antibodies against AFP. After the terminating of the incubation the gel was washed out with 0.1 M bicarbonate buffer pH 8.3 and AFP was eluted with 0.05 M glycine-HCl buffer, pH 2.5. The eluate was then chromatographically purified of ballast proteins. The column contained 25 ml Sepharose® with immobilized polyclonal antibodies against normal human blood proteins (1 mg/ml for packed gel). The eluate containing AFP was concentrated followed by applying on Sephacryl® S-200 (column 1.5×120 cm). The eluated AFP was lyophilized. The AFP preparation thus obtained was more than 99% purity not containing low-molecular weight impurities and completely retaining the biological activity.

The immunoaffinity matrix for AFP isolation was prepared by means of immobilising anti-AFP monoclonal antibodies isolated from mouse ascite liquid (AFP-Ab) on BrCN-Sepharose®. 30 mg AFP-Ab dissolved in 10 ml bicarbonate buffer were then added to 25 ml condensed BrCN-Sepharose® and incubated for 1 hr at room temperature. The obtained AFP-Ab-Sepharose® was washed with 0.5 l bicarbonate buffer. The affinity matrix contained about 1 mg AFP-Ab per 1 ml condensed gel.

The immunoaffinity matrix for AFP purification of serum proteins was prepared by means of immobilizing polyclonal antibodies against normal human serum proteins on BrCN-Sepharose®. 30 mg antibodies dissolved in 10 ml bicarbonate buffer were then added to 25 ml condensed BrCN-Sepharose® and incubated for 1 hr at room temperature. The obtained immunosorbent was washed with 0.5 l bicarbonate buffer. The final affinity matrix contained about 1 mg immobilized antibodies per 1 ml condensed gel.

Example 2

N-AAP Synthesis 305 mg (1 mmol) arachidonic acid (Sigma Chemical Co.) was dissolved in 3 ml acetonitrile containing 0.14 ml triethylamine. The mixture was cooled down to −15° C. followed by adding 130 ml butyl-formiate and incubated at the given temperature. 30 min after the precipitated triethylamine hydrochloride was separated. Thus obtained the solution of mixed anhydride was then added to a 1 ml methanol containing 0.12 ml thanol-amine. The mixture was stirred for 15 min at 0° C. and then transferred into room temperature. 2 hr after the mixture was diluted with 10 ml of 1N HCl and extracted by ether (2×20 ml). The ether extraction was washed with water and then dried over anhydrous sodium sulfate. The solution was then evaporated to dryness and the substance was dissolved in 5 ml acetone and subjected to a 2 cm-high aluminium oxide column (10 g, basic, 11 grade acc. to Brockman). The column was washed with 30 ml acetone. The eluate was evaporated and further dried under vacuum pressure. Thus obtained N-arachidonoyl-ethanolamine was shown to be pure as judged from silica gel TLC data (benzenedioxane-acidic acid, 25:5:1). Then 5 ml pyridine containing 400 mg pyridinium 2-cyanoethyl phosphate were added followed by 620 mg dicyclohexyl carbodiimide. The flask was filled with argon and the mixture was kept at room temperature for 20 hr. After that 1 ml water was added and stirred for extra 30 min. The precipitated N,N-dicyclohexyl-urea was separated via filtration, water and pyridine were evaporated. The reaction product arachidonoyl aminoethyl, 2-cyanoethyl phosphate was purified by silica gel column chromatography washing the column with chloroform-methanol mixtures with increasing methanol content. The fraction were subjected to TLC (chloroform-methanol-water, 65.25:4, $R_f$=0.63) and those fractions being positively stained after spraying the plates with phospholipid detecting reagent were joined, dried, and dissolved in 1.5 ml tetrahydrofuran. The obtained solution was added by drops to 5 ml 1N NaOH, pre-cooled at 0° C. After 20 min stirring the pH was adjusted to 2–3 and then the mixture was extracted with chloroform-methanol 2:1 (v/v). The extraction was washed with methanol-water 10:9, evaporated and subjected to silica gel column chromatography washing the column with chloroform-methanol mixtures with increasing methanol content. The fractions were subjected to TLC (chloroform-methanol-water, 65:25:4, v/v/v, Rf=0.3) and those being positively stained after spraying the plates with phospholipid detecting reagent were joined and dried. The final outcome of arachidonoyl aminoethylphosphate (N-AAP) was 150 mg (35%). Calculated: P 7.26. Found. P 7.14. IR-spectrum (film: v, cm-1) 1070, 1220, 1555, 1650. H-NMR (d, $CDCl_3$) 0.88 (3H, t, $CH_3$), 1.30 (8H, s, $CH_2$), 2.00–2.40 (6H, m, 2 groups $CH_2CH=CH$ and $CH_2CO$), 2.70–2.90 (6H, wid. s, $3CH=CHCH_2CH=CH$), 3.48 (2H, t, $NCH_2$), 5.24–5.44 (8H, m, CH=CH).

Example 3

AFP Binding with N-AAP

To determine N-AAP affinity to human AFP a competitive substitution of [5, 6, 8, 9, 11, 12, 14, 15-$^3$H] arachidonic from the protein's binding site was used. To tubes containing 0.05 nM AFP in 1 ml 0.1 M bicarbonate buffer and 0.7 nM [3H] arachidonic acid and the increasing amounts of arachidonic acid or N-AAP (5–5000 nM) were added. The tubes were incubated for 2 hr at room temperature. To separate protein-bound and free fractions of [3H] arachidonic acid 0.5 ml of 0.5% suspension of activated carbon was added to each tube and incubated at 4° C. for 30 min. The carbon was sedimented by centrifugation at 3000 g, aliquots were added to 10 ml scintillating mixture and the vials were measured in beta-counter.

The binding parameters of arachidonic acid and N-AAP and the number of binding sites per protein molecule were calculated according to Scatchard (Scatchard O., Ann. N.Y. Acad. Sci. 51., p 660–664, 1949).

Based on three independent determinations Ka for AFP with arachidonic acid was found to be $6 \cdot 10^7$ $M^{-1}$ and n>1.2. For N-AAP the inhibition binding constant of arachidonic acid with AFP ($K_1$) was $3 \cdot 10^6$ $M^{-1}$.

Example 4

Preparation of N-AAP Complex with Human AFP 50 mg AFP (0.75 mmol) was dissolved in 150 ml physiological solution. 35 mg (~75 mmol) N-AAP dissolved in 5 ml ethanol was added to the obtained solution. The mixture was incubated for 30 min at room temperature (20–25° C.). The obtained complex of N-AAP with AFP was concentrated to 10 ml using Sartocon® Micro "Sartorius" for high-molecular weight compounds with a 20.000 Da membrane cut off. The final solution was sterilized with a syringe tip Minisart® SRP Syringe Filter, "Sartorius" a membrane of $0.22\mu$ pore size. A sterilized concentrated preparation was distributed in 10 vials of 1 ml each. The vials were blown with argon stream, closed firmly and stored at 4–8° C.

Example 5

AFP Influence on Humoral Immune Response

AFP was administered intravenously to 10 mouse males of CBA line (weight 18–22 g) in a dose of 0.009 mg per capita. Simultaneously 5% sheep erythrocytes suspension was injected peritoneally (0.2 ml per capita) to both control and experimental animals. The control animals were also injected with the equal volume of NaCl isotonic solution intravenously.

The effect of AFP on humoral immune response was analyzed by counting the quantity of AFC in the spleen according to Cunningham (Cunningham A. J., Nature, v.207, p. 1106–1107, 1965) (per $10^6$ spleen cells and per spleen).

It was shown that the administered dosage of AFP resulted in 30% lower relative amount of AFC on the 5-th day after injection of sheep erythrocytes suspension in comparison with control group (366.2±40.8 for control animals and 255.5±13, for experimental series, per $10^6$ cells, P<0.05). However the total AFC amount has not significantly changed (27.2±5.7 $10^3$ per spleen for control group and 23.6±1.5 $10^3$ for experimental series, P>0.05).

Example 6

N-AAP Influence on Humoral Immune Response

N-AAP was administered intravenously to 10 mouse males of CBA line (weight 18–22 g) in a dose of 0.09 mg per capita Simultaneously 5% sheep erythrocytes suspension was injected peritoneally (0.2 ml per capita). Control series were injected with 0.15 ml NaCl isotonic solution intravenously. The effect of N-AAP on humoral immune response was analysed by counting the quantity of AFC in the spleen according to Cunningham (per $10^6$ spleen cells and per spleen).

The relative amount of AFC on the 5-th day after injection was 366.2±40.8 for control animals and 342.2±28.5 for experimental series, P>0.05. The total AFC amount was 27.2±5.7 $10^3$ for control group and 36.0±8.7 $10^3$ for experimental series, P>0.05. The obtained data shows that N-AAP itself has no immunogenic activity in itself.

Example 7

AFP/N-AAP Complex (1:200) Influence on Humoral Immune Response 0.15 ml AFP/N-AAP complex was administered intravenously to 10 mouse males of CBA line (weight 18–22 g) in a dose of 0.009 mg AFP and 0.09 mg N-AAP per capita. Simultaneously 5% sheep erythrocytes suspension was injected peritoneally (0.2 ml per capita). Control series were intravenously injected with equal volumes of NaCl isotonic solution. The effect of the AFP/N-AAP complex on humoral immune response was analyzed by counting the quantity of AFC in the spleen according to Cunningham (per $10^6$ spleen cells and per spleen).

The relative amount of AFC on the 5-th day after injection was 366.2±40.8 for control animals and 686.7±89.5 for experimental series, P<0.05. The total AFC amount was 27.2±5.3 $10^3$ for control group and 71.0±18.7 10 3 for experimental series, P<0.05.

Thus, the relative amount of AFC on the 5-th day after injection increased 87%, and the total AFC amount increased 162% in comparison with the amount of cells in the animals immunized only with sheep erythrocytes. The data obtained proved that in those animals receiving AFP (0.009 mg per capita, see example 5) combined with sheep erythrocytes injections the relative amount of AFC increased 169% and total AFC amount 203%.

Example 8

AFP/N-AAP Complex (1:100) Influence on Humoral Immune Response 0.15 ml AFP/N-AAP complex was administered intravenously to 10 mouse males of CBA line (weight 18–22 g) in a dose of 0.009 mg AFP and 0.045 mg N-AAP per capita. Simultaneously 5% sheep erythrocytes suspension was injected peritoneally (0.2 ml per capita). Control series were intravenously injected with equal volumes of NaCl isotonic solution. The effect of the AFP/N-AAP complex on humoral immune response was analyzed by counting the quantity of AFC in the spleen according to Cunningham (per $10^6$ spleen cells and per spleen).

The relative amount of AFC on the 5-th day after injection was 366.2±40.8 for control animals and 476.2±28.1 for experimental series, P<0.05. The total AFC amount was 27.2±5.7 $10^3$ for control group and 48.0±6.2 $10^3$ for experimental series, P<0.05.

Thus, the apparent amount of AFC on the 5-th day after injection increased 30%, and total AFC amount increased 79% in comparison with amount of cells in the animals immunized only with sheep erythrocytes. The data obtained proved that in those animals receiving AFP (0.009 mg per capita, see example 5) combined with sheep erythrocytes injections the apparent amount of AFC increased 86.6% and total AFC amount 103.4%.

Example 9

AFP/N-AAP Complex (1:300) Influence on Humoral Immune Response 0.15 ml AFP/N-AAP complex was administered intravenously to 10 mouse males of CBA line (weight 18–22 g) in a dose of 0.009 mg AFP and 0.135 mg N-AAP per capita. Simultaneously 5% sheep erythrocytes suspension was injected peritoneally (0.2 ml per capita) Control series were intravenously injected with equal volumes of NaCl isotonic solution. The effect of the AFP/N-AAP complex on humoral immune response was analyzed by counting the quantity of AFC in the spleen according to Cunningham (per $10^6$ spleen cells and per spleen).

The relative amount of AFC on the 5-th day after injection was 366.2±40.8 for control animals and 543.2±50.2 for experimental series, $P<0.05$. The total AFC amount was 27.2±5.7 $10^3$ for the control group and 55.3±5.3×$10^3$ for the experimental series, $P<0.05$.

Thus, the relative amount of AFC on the 5-th day after injection increased 48.3%, and total AFC amount increased 103% in comparison with amount of cells in the animals immunized only with sheep erythrocytes. The data obtained proved that in those animals receiving AFP (0.009 mg per capita, see example 5) combined with sheep erythrocyte injections the relative amount of AFC increased 112.8% and total AFC amount 134.3%.

Experimental Part Added during the Priority Year:

In order to determine the molar ratio between AFP and N-AAP in the complexes, ultrafiltration or (and) gel-chromatography in the presence of [$^3$H]-N-AAP was performed. The present inventor carried out gel exclusion chromatography of the AFP complexes with N-AAP at different concentrations of components—1 mole AFP per 800, 1600 and 2400 moles N-AAP, for estimation of the AFP maximum binding capacity. Obtained data indicate that the ratio AFP/N-AAP in the complexes is between 1/100 and 1/300. In addition, these molar ratios AFP/N-AAP in the complexes depend on the initial concentrations of components in the solution. Thus, initial concentrations of 1 mole AFP per 800 moles N-AAP gives a ratio close to 1/100 (AFP/N-AAP) in the complex; concentrations of 1 mole AFP per 1600 moles N-AAP gives a ratio close to 1/200 (AFP/N-AAP) in the complex; concentrations of 1 mole AFP per 2400 moles N-AAP gives a ratio close to 1/300 (AFP/N-AAP) in the complex.

Example 10

N-AAP Synthesis

Arachidonic acid (152 mg, 0.5 mmol) and triethylamine (52 mg, 0.51 mmol) were dissolved in 3 ml of dry acetonitrile and chilled to −15° C., and 70 mg (0.51 mmol) of butyl chloroformate was added. After 30 min, the mixture free of the precipitated triethylamine hydrochloride was pipetted in a solution of 2-aminoethanol (61 mg, 1 mmol) in 1 ml of methanol, stirring was continued for 15 min at −15° C., then the mixture obtained was allowed to warm to room temperature. After 2 h, 0.5 M HCl was added, and the mixture was extracted with ether (20 ml). The extract was washed with water, then dried with $Na_2SO_4$, and evaporated under reduced pressure. The residue was dissolved in 2 ml of chloroform and purified by column (2×2 cm) chromatography on aluminium oxide (basic, Brockmann II). Elution of the column with chloroform—methanol (9:1 v/v) and evaporation of the appropriate fractions gave 165 mg (95%) of desired N-arachidonoylaminoethan-2-ol as oil: TLC [benzene-dioxan-acetic acid (25:5:1 v/v/v)] $R_f$ 0.4.

A solution of pyridinium cyanoethylphosphate (2 mmol) in anhydrous pyridine (3 ml) was added to dry N-acylaminoethan-2-ol. N,N'-Dicyclohexylcarbodiimide (413 mg, 2 mmol) was then added and the mixture was stirred at room temperature. After 20 h, the mixture was cooled to 0° C., water (0.5 ml) was added and, after stirring for 30 min at room temperature, the precipitated N,N'-dicyclohexylurea was separated by filtration. The filtrate was evaporated under reduced pressure and the residue obtained was fractionated by short column chromatography on silica gel. The desired phosphorylated N-acylaminoalcohol was eluted from the column with chloroform—methanol (70–60:30–40, v/v). The composition of the eluates was controlled by TLC on Silica gel 60 plates [chloroform-methanol-$NH_3$ aq (9:7:2,v/v/v)] using a molybdate spray for detecting the spots. The appropriate fractions were combined, evaporated to dryness in vacuo and residue was dissolved in 1 ml tetrahydrofuran. That solution was added, dropwise over a period of 5 min, to a cooled (ice-bath), stirred 1.5 M NaOH aq (4 ml). After a further 25 min, the mixture was acidified with 1 N HCl to pH 2–3 and extracted with chloroform—methanol (2:1, v/v). The extract was washed with methanol—water (10:9, v/v), concentrated in vacuo and applied to a column of silica gel. The desired product was eluted from column with chloroform—methanol (30–20:70–80, v/v), the fractions containing pure substance stained on the TLC plates with molybdate spray were combined and evaporated to dryness to give 88 mg (41%) of (N-AAP): $R_f$ 0.10–0.15 [chloroform-methanol-$NH_3$aq (9:7:2 v/v/v)]; $^1$H-NMR ($CD_3SOCD_3$, 200 MHz) δ0.9–1.0 (t, 3H, ω-$CH_3$); 1.3 (s, 8H, 4$CH_2$); 2.0–2.4 (m, 6H, 2$CH_2$CH=CH and $CH_2$CO); 2.7–2.9 (br s, 6H, 3HC=CHC$H_2$CH=CH); 3.4–3.5 (br s, 2H, $CH_2$NH); 3.9–4.0 (br s, 2H, $CH_2$OP); 5.2–5.4 (br s, 8H, 4HC=CH); 8.2–8.4 (m, 3H, NH and 2POH).

Example 11

Determination of the Molecular Weight of the Human-AFP-NAA-P Complex

Sephacryl® S-300-HR and gel filtration molecular weight markers, i.e. proteins having a range of molecular weights from 29 kD to 700 kD (the MW-GF-1000 kit) were purchased from Sigma Chemical Co. [5, 6, 8, 9, 11, 12, 1 15-$^3$H] arachidonic acid was purchased from Amersham International, UK. A gel filtration column (1.0×90 cm) with Sephacryl® S-300-HR was standardised with these proteins as molecular weight markers. 50 mM sodium phosphate buffer (pH 7.4) containing 100 mM NaCl was used as equilibration buffer in the testing.

Samples of complexes of AFP (0.5 mg) with different amounts of N-AAP (2.5 mg, 5 mg and 7.5 mg) in the volume 0.5 ml were analyzed on the standardised column with Sephacryl® S-300-HR. Detection of AFP complexes was carried out by measuring the absorbance at 280 nm or counting if the radioactive label [$^{125}$I] had been incorporated into the AFP molecule and [$^3$H] into N-AAP.

It was shown that the complexes of AFP and N-AAP elutes from a molecular exclusion column at the positions equivalent to these of the proteins whose molecular weights are in the range from 120 kD to 180 kD. This data indicates that the ratio AFP/N-AAP in the complexes is about 1/100–300 moles, accordingly.

Example 12

Rat AFP/N-AAP complex (1:200) Influence on Humoral Immune Response

Rat AFP was isolated from neonatal rat serum. Monospecific anti-rat serum alpha-fetoprotein IgG was coupled to cyanogen bromide-activated Sepharose 4B (4.5 mg/ml packed volume of gel) to yield an immunoaffinity matrix. Acidic elution condition were as described previously (Calvo, M., et al., J. Chromatogr. V.328, p.392–395, 1985). Similar to human AFP the complexes of rat AFPIN-AAP reveal strong effect on humoral immune response in mice (example 11). Thus, the relative amount of AEC on the 5-th day after injection increased 195% and total AEC amount increased 175% in comparison with amount of the cells in the animals immunized only with sheep erythrocytes. These experiments allow drawing a conclusion that both human AFPIN-AAP complexes and rat AFPIN-APP complexes could be use as effective therapeutic preparations. Analogous preparation would be create if use AFP from some other animals, cell culture, genetically modified AFP. It is necessarily to take into account several reasons: cost, availability, risk of viral infections, possibilities to obtain authorisation for the production etc., in any specific case.

In order to determine the effect of the inventive complex, 0.15 ml AFP/N-AAP complex was administered intravenously to 10 mouse males of CBA line (weight 18–22 g) in the dose of 0.009 mg rat AFP and 0.09 mg N-AAP per capita. Simultaneously 5% sheep erythrocytes suspension was injected peritoneally (0.2 ml per capita). Control series were injected intravenously with equal volumes of isotonic NaCl solution. The effect of rat AFP/N-AAP complex on humoral immune response was analyzed by counting the quantity of AFC in the spleen according to Cunningham (per $10^6$ spleen cells and per spleen).

The relative amount of AFC on the 5-th day after injection was 338.8±67.9 for control animals and 659±38.4 for experimental series, P<0.05. The total AFC amount was 51.2±13.5·$10^3$ for the control group and 89.4±11.8·$10^3$ for the experimental series, P<0.05. Rat AFP exhibits no immunogenic activity. The relative amount of AFC was 425.1±42.1 for control animals and 428.1±11.5 for experimental series, P>0.05. The total AFC amount was 65.4±6.8·$10^3$ for the control group and 60.3±13.5·$10^3$ for the experimental series, P>0.05.

Thus, the relative amount of AFC on the 5-th day after injection increased 195%, and total AFC amount increased 175% in comparison with amount of cells in the animals immunized only with sheep erythrocytes.

Example 13

Toxicity Studies

The toxicity of N-AAP was studied in random breed male mice (19–24 g). A water solution of N-AAP was injected once slowly in the tail vein of mice in a range of doses 40–70 mg/kg. Each group of mice included 6 animals, at least The assessment of acute toxicity was carried out according to the method of Litchfield et al. (Litchfield J. T., Wilcoxon F., J. Pharmacol. Exptl. Therap., Vol.96, P. 99–103, 1949). The acute toxicity of N-AAP was shown to be as follows:

| | |
|---|---|
| $DL_{50}$ = | 63 (54.8 ÷ 72.5) mg/kg at p = 0.05; |
| $DL_{10}$ = | 46 mg/kg; |
| $DL_{90}$ = | 87 mg/kg |

The therapeutic index is 10.

The present inventor tested AFP/N-AAP complexes at the ratios—1/100, 1/200 and 1/300 in order to estimate the influence of these complexes on humoral immune response in mice (examples 8–10). All presented complexes reveal biological activity in all experiments. The complex AFP/N-AAP was shown to have a more powerful effect on humoral immune response, at the ratio 1:200 mole/mole.

Although the invention has been described with regard to its preferred embodiments, which constitute the best mode presently known to the inventors, it should be understood that various changes and modifications as would be obvious to one having the ordinary skill in this art may be made without departing from the scope of the invention which is set forth in the claims appended hereto.

I claim:

1. An equilibrium reversible complex comprising alpha-fetoprotein (AFP) and arachidonoyl aminoethyl phosphate (N-AAP) in a concentration at least equal to the critical micelle concentration.

2. The equilibrium reversible complex according to claim 1, wherein the concentration of N-AAP is between 100 and 300 moles per AFP.

3. The equilibrium reversible complex according to claim 2, wherein the concentration of N-AAP is about 200 moles per AFP.

4. The equilibrium reversible complex according to claim 1, wherein the AFP is human AFP isolated from human cord serum.

5. The equilibrium reversible complex according to claim 2, wherein the AFP is human AFP isolated from human cord serum.

6. The equilibrium reversible complex according to claim 3, wherein the AFP is human AFP isolated from human cord serum.

7. The equilibrium reversible complex according to claim 1, wherein the AFP is human AFP and is isolated from a cell culture of AFP producing cells.

8. The equilibrium reversible complex according to claim 3, wherein the AFP is human AFP and is isolated from a cell culture of AFP producing cells.

9. The equilibrium reversible complex according the claim 3, wherein the AFP is human AFP and is isolated from a cell culture of AFP producing cells.

10. The equilibrium reversible complex according to claim 1 for use as a therapeutic agent for enhancing humoral immune response.

11. The equilibrium reversible complex according to claim 2 for use as a therapeutic agent for enhancing humoral immune response.

12. The equilibrium reversible complex according to claim 3 for use as a therapeutic agent enhancing humoral immune response.

13. The equilibrium reversible complex according to claim 4 for use as a therapeutic agent for enhancing humoral immune response.

14. The equilibrium reversible complex according to claim 1 for use as an agent for the treatment of immune deficiencies occurring as a consequence of cancer therapy.

15. The equilibrium reversible complex according to claim 14 wherein the immune deficiency is neutropenia.

16. The equilibrium reversible complex according to claim 2 for use as an agent for the treatment of immune deficiencies occurring as a consequence of cancer therapy.

17. The equilibrium reversible complex according to claim 3 for use as an agent for the treatment of immune deficiencies occurring as a consequence of cancer therapy.

18. The equilibrium reversible complex according to claim 4 for use as an agent for the treatment of immune deficiencies occurring as a consequence of cancer therapy.

19. A lyophilized preparation comprising an equilibrium reversible complex according to claim 1.

20. An injectable solution comprising a therapeutically significant amount of an equilibrium reversible complex according to claim 1.

21. A pharmaceutical composition comprising an equilibrium reversible complex according to claim 1 for the treatment of immune deficiencies occurring as a consequence of cancer therapy.

* * * * *